(12) United States Patent
Chauhan et al.

(10) Patent No.: US 7,440,793 B2
(45) Date of Patent: Oct. 21, 2008

(54) APPARATUS AND METHOD FOR REMOVING ABNORMAL TISSUE

(76) Inventors: Sunita Chauhan, Blk 27, #27-02-518, Hall of Residence-IV, 10 Nanyang Drive, Nanyang Tech. University Campus, Singapore 637720 (SG); Ranjan Kumar Mishra, Blk 863, #05-501, Jurong West Street 81, Singapore 640863 (SG); Siew Bock Wee, 22, Oei Tiong Ham Park, Singapore 267027 (SG); Mona P. Tan, 4, Bedok Terrace, Singapore 469163 (SG)

( * ) Notice: Subject to any disclaimer, the term of this patent is extended or adjusted under 35 U.S.C. 154(b) by 308 days.

(21) Appl. No.: 10/896,752

(22) Filed: Jul. 22, 2004

(65) Prior Publication Data

US 2006/0020279 A1    Jan. 26, 2006

(51) Int. Cl.
*A61B 5/05* (2006.01)
*A61B 8/00* (2006.01)
*A61N 1/30* (2006.01)

(52) U.S. Cl. ................ 600/424; 600/429; 600/437; 604/19

(58) Field of Classification Search ............ 600/437, 600/424; 604/19; 382/128
See application file for complete search history.

(56) References Cited

U.S. PATENT DOCUMENTS

| | | | |
|---|---|---|---|
| 5,078,140 A * | 1/1992 | Kwoh ................ 600/417 |
| 5,595,185 A | 1/1997 | Erlich | |
| 5,647,373 A * | 7/1997 | Paltieli ................ 600/567 |
| 6,019,733 A | 2/2000 | Farascioni | |
| 6,109,270 A * | 8/2000 | Mah et al. ............ 606/130 |
| 6,119,033 A | 9/2000 | Spigelman et al. | |
| 6,213,957 B1 | 4/2001 | Milliman et al. | |
| 6,234,177 B1 | 5/2001 | Barsch | |
| 6,494,844 B1 * | 12/2002 | Van Bladel et al. ...... 600/567 |
| 6,892,112 B2 * | 5/2005 | Wang et al. .......... 700/258 |
| 2004/0015070 A1 * | 1/2004 | Liang et al. .......... 600/407 |
| 2004/0171933 A1 * | 9/2004 | Stoller et al. ......... 600/427 |

OTHER PUBLICATIONS

Goedde, Timothy, "overview of Minimally Invasive Breast Biopsies—Device Evolution More Efficient and Effective", Suros Surgical Systems Inc., Apr. 2004, pp. 1-16, Rev. 2.

Hasselgren, P. et al., "Breast Biopsy with Needle Localization: Accuracy of Specimen X-ray and Management of Missed Lesion", Surgery, Oct. 1993, 114(4), Abstract.

Yim, J.H. et al., "Mammographically Detected Breast Cancer. Benefits of Stereotactic Core Versus Wire Localization Biopsy", Annals of Surgery, Jun. 1996, 223(6), Abstract.

(Continued)

*Primary Examiner*—Eric F Winakur
*Assistant Examiner*—Michael T. Rozanski
(74) *Attorney, Agent, or Firm*—Dinsmore & Shohl LLP

(57) ABSTRACT

A computer assisted, minimally invasive method and apparatus for surgically removing abnormal tissue from a patient, for example, from a breast, are disclosed. The method involves imaging of the breast to locate the abnormal tissue, and determining a volume encapsulating the abnormal tissue and including a margin of healthy tissue. Based on the volume, a sequence of movements of a surgical instrument for tissue removal device is planned, so as to predictably excise the desired volume of tissue.

30 Claims, 11 Drawing Sheets

FIG. 1

OTHER PUBLICATIONS

Ferzli, G.S. et al., "Advanced Breast Biopsy Instrumentation: A Critique", Journal of the American College of Surgeons, Elsevier Science Inc., 1997, pp. 154-160, vol. 185, No. 2.

Estoesta, J.V. et al., "BreastScreen New South Wales Ten Year Statistical Report: 1988-1998", Sydney, BreastScreen NSW, 2000.

Mammotome Breast Biopsy System for Breast Health and Care:, <http://breastbiopsy.com/mammotome.jsp>.

"FDA Clears Minimally Invasive Method for Management of Non-Cancerous Breast Lumps", <http://ethiconendo.com/pr/pressrelease9.jsp>.

* cited by examiner

APPARATUS AND METHOD FOR REMOVING ABNORMAL TISSUE

FIELD OF THE INVENTION

The present invention relates generally surgical apparatus and methods, and more particularly to an apparatus and method for removing abnormal tissue. The apparatus and methods are particularly well suited for removing abnormal breast tissue.

BACKGROUND OF THE INVENTION

In most countries, breast cancer is the second most prevalent cancer to afflict women. Currently, abnormal breast tissue is detected by various methods, such as physical breast examination, mammography, ultrasound and other breast imaging methods.

In order to determine whether such abnormalities are benign or malignant, examination of the histopathology of the abnormal tissue is required. Therefore, a sample of the abnormal tissue is taken by biopsy and is analysed by microscopic evaluation.

At present, there are biopsy techniques that can be performed through a small incision in the affected breast, and which are therefore considered to be minimally invasive. Typically, a radiologist or surgeon removes a sample of breast tissue and sends it to a pathological laboratory for microscopic examination. Minimally invasive techniques for breast biopsy include fine needle aspiration (FNA), core needle biopsy, large core surgical (ABBI) and vacuum-assisted biopsy (Mammotome or MIBB).

Minimally invasive biopsies may use computer-generated images to locate breast abnormalities, including the use of x-ray and ultrasound generated images. By accurately pinpointing and mapping the area to be biopsied, a small sample can easily be taken from the abnormal tissue.

The existing biopsy methods are limited to one or at most a few sample removals, and are not designed, nor are intended, to perform surgical excision of the abnormality. In some cases the biopsy method is limited to the removal of just enough cells or fluid sufficient for pathological testing.

If the abnormality is confirmed to be cancerous, typically the abnormal tissue, as well as a surrounding margin of healthy tissue, is removed. Surgical methods typically involve either a lumpectomy, which involves removal of the abnormality and surrounding tissue while leaving the majority of the breast tissue intact, or a mastectomy, which involves removal of all or a large portion of the breast tissue. Surgical removal may be done in combination with other treatments, such as chemotherapy or radiation treatment.

The advent of screening mammography has led to a paradigm shift in the presentation of breast cancers, with a higher proportion of tumours diagnosed at an impalpable stage. These lesions are smaller in size, and breast conservation treatment would be appropriate for these cancers. Breast conservation therapy involves the removal of the cancer, together with a margin of surrounding normal tissue, followed by a secondary treatment as necessary.

Surgical methods typically require stitches to close the excision and can leave a scar, which may complicate the interpretation of follow up breast examinations; increase the chance of bleeding, and infection; and cause problems with wound healing. As well, there are mortality risks associated with the use of anaesthesia.

Clearly then, there is a need for minimally invasive surgical methods for effective removal of abnormal tissue from a breast.

SUMMARY OF THE INVENTION

A computer assisted, minimally invasive method of surgically removing abnormal tissue from a patient, for example, from a breast, is provided. The method involves imaging of the breast to locate the abnormal tissue, and determining a volume encapsulating the abnormal tissue and including a margin of healthy tissue. Based on the volume, a sequence of movements of surgical instrument is planned, so as to excise the desired volume of tissue.

In one embodiment, an automated device, combining an imaging probe attached to a robotic imaging arm and a tissue removal device attached to a robotic surgical arm, controlled by a central control system, suitable for surgically removing abnormal tissue from a breast, is provided. The control system may drive the movements of both the imaging arm and the surgical arm, and receives and processes the image data so as to determine the sequence of movements necessary to excise the volume of tissue desired.

Methods exemplary of the invention use the apparatus to provide an assisted or automated surgical method for removing abnormal tissue, such as a tumour, from a breast, and which limit the volume of tissue removed and the size of the incision or incisions made, so as to reduce scarring and deformation of the remaining tissue. The method is particularly suitable for small breast tumours and abnormalities that are localized and intact (e.g. carcinomas in situ). It can be performed using a local anaesthetic on an outpatient basis, eliminating the cost and risk associated with current lumpectomy and mastectomy procedures.

In accordance with an aspect of the present invention, there is provided a computer-assisted method of removing abnormal tissue from a region of interest. The method includes generating a three-dimensional (3-D) map of the region of interest including abnormal tissue, and determining a tissue volume, based on the 3-D map. The tissue volume includes the abnormal tissue and an adjacent margin of healthy tissue. The method further includes determining, based on the volume, a set of coordinates locating at least one incision point and a series of excision points associated with the incision point, and controlling movement of a surgical instrument used to excise tissue, to sequentially move to the incision point and the series of excision points and excise tissue, resulting in removal of the tissue volume.

In accordance with another aspect of the invention, there is provided an apparatus for tissue removal, including a robotic imagining arm for holding and moving an imaging probe, and a robotic surgical arm for holding and moving a surgical instrument suitable for tissue removal. A computing device controls movements of the robotic imaging arm, the imaging probe, the robotic surgical arm, and the surgical instrument. The computing device is operable to generate a three-dimensional (3-D) map of the tissue including abnormal tissue; to determine a tissue volume, based on the map, the tissue volume including the abnormal tissue and an adjacent margin of healthy tissue; and to determine a set of coordinates, including an incision point and a series of excision points associated with the incision point to move a tissue removal device to the incision point and the series of excision points and excise tissue to remove the volume, resulting in removal of the abnormal tissue.

In accordance with yet another aspect of the invention, there is provided a computer-readable medium storing processor-executable instructions which, when executed by a processor of a control system of a surgical apparatus including a robotic imaging arm for holding and moving an imaging probe and a robotic surgical arm for holding and moving a surgical instrument, adapt the control system to generate a three-dimensional (3-D) map of the tissue including abnormal tissue, and to determine a tissue volume, based on the map, the tissue volume including the abnormal tissue and an adjacent margin of healthy tissue. The control system is also adapted to determine a set of coordinates, including an incision point and a series of excision points associated with the incision point, based on the tissue volume to move a surgical instrument sequentially to the incision point and the series of excision points and excise tissue to remove the volume, resulting in removal of the abnormal tissue.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
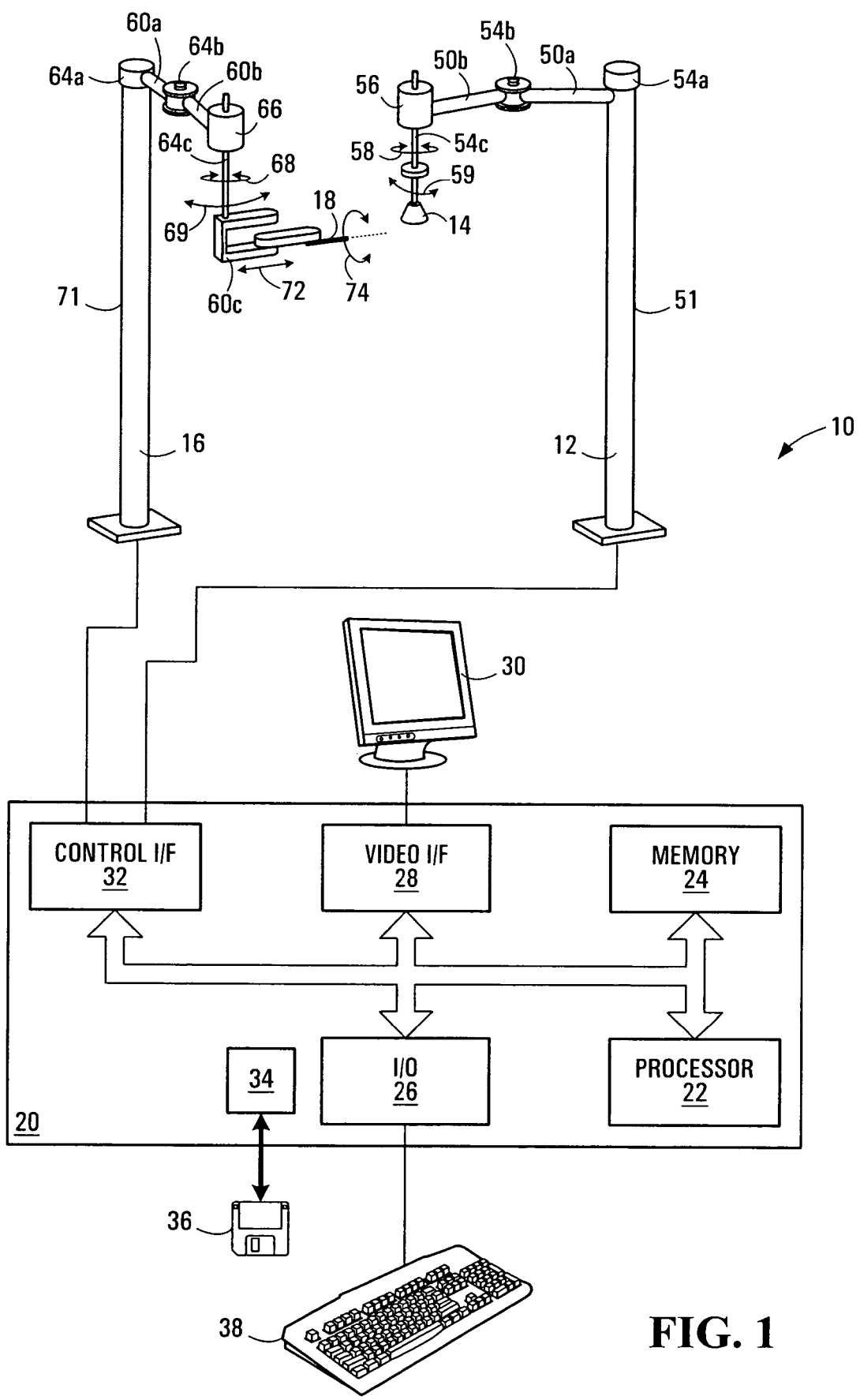
FIG. 1 is a schematic block diagram of an automated surgical apparatus, exemplary of an embodiment of the present invention.

FIG. 1 illustrates an apparatus 10 for removing abnormal tissue from the breast of a patient, exemplary of an embodiment of the present invention.

In this context, the term "abnormal tissue" refers to tissue, which may be benign or malignant, and includes cysts, lumps, microcalcifications, spiculated masses, and asymmetric densities, and which may be palpable or non-palpable. Other abnormal tissue may be part of localized tumors, including carcinoma—in situ, such as Fibroadenomas, Phyllodes tumours, which are benign breast tumors in the glandular and stroma (connective), Fat necrosis (a benign condition where fatty breast tissue swells or becomes tender) as well as malignant breast tumours such as Lobular Carcinoma in situ (LCIS), Ductal Carcinoma in situ (DCIS), preferably at Stage-0 and I.

As illustrated, apparatus 10 includes a robotic imaging arm 12 for holding and moving an imaging probe 14; and a robotic surgical arm 16 for holding and moving a minimally invasive surgical instrument 18.

Arms 12 and 16 are interconnected with computing device 20 acting as a control system for computerized control and movement of these arms 12, 16. Imaging output of imaging probe 14 is similarly provided to computing device 20.

A simplified preferred hardware architecture of an example computing device 20 is schematically illustrated in FIG. 1. In the illustrated embodiment, device 20 is a conventional computing device. Device 20 could, for example, be an Intel x86 based computer acting as a Microsoft Windows NT, Apple, or Unix based server, workstation, personal computer or the like. Example device 20 includes a processor 22, in communication with computer storage memory 24; input output interface 26; and video adapter 28. As well, device 20 may optionally include a display 30 interconnected with adapter 28; input/output devices, such as a keyboard 38 and disk drive 34 and a mouse (not shown) or the like. Device 20 further includes a control input/output interface for providing typical control signal inputs and outputs to actuate servo motors, and to read position sensors. Processor 22 is typically a conventional central processing unit, and may for example be a microprocessor in the INTEL x86 family. Of course, processor 22 could be any other suitable processor known to those skilled in the art. Computer storage memory 24 includes a suitable combination of random access memory, read-only-memory, and disk storage memory used by device 20 to store and execute software programs adapting device 20 to function in manners exemplary of the present invention. Drive 34 is capable of reading and writing data to or from a computer readable medium 36 used to store software and data to be loaded into memory 24. Computer readable medium 36 may be a CD-ROM, diskette, tape, ROM-Cartridge or the like.

Figure 2:
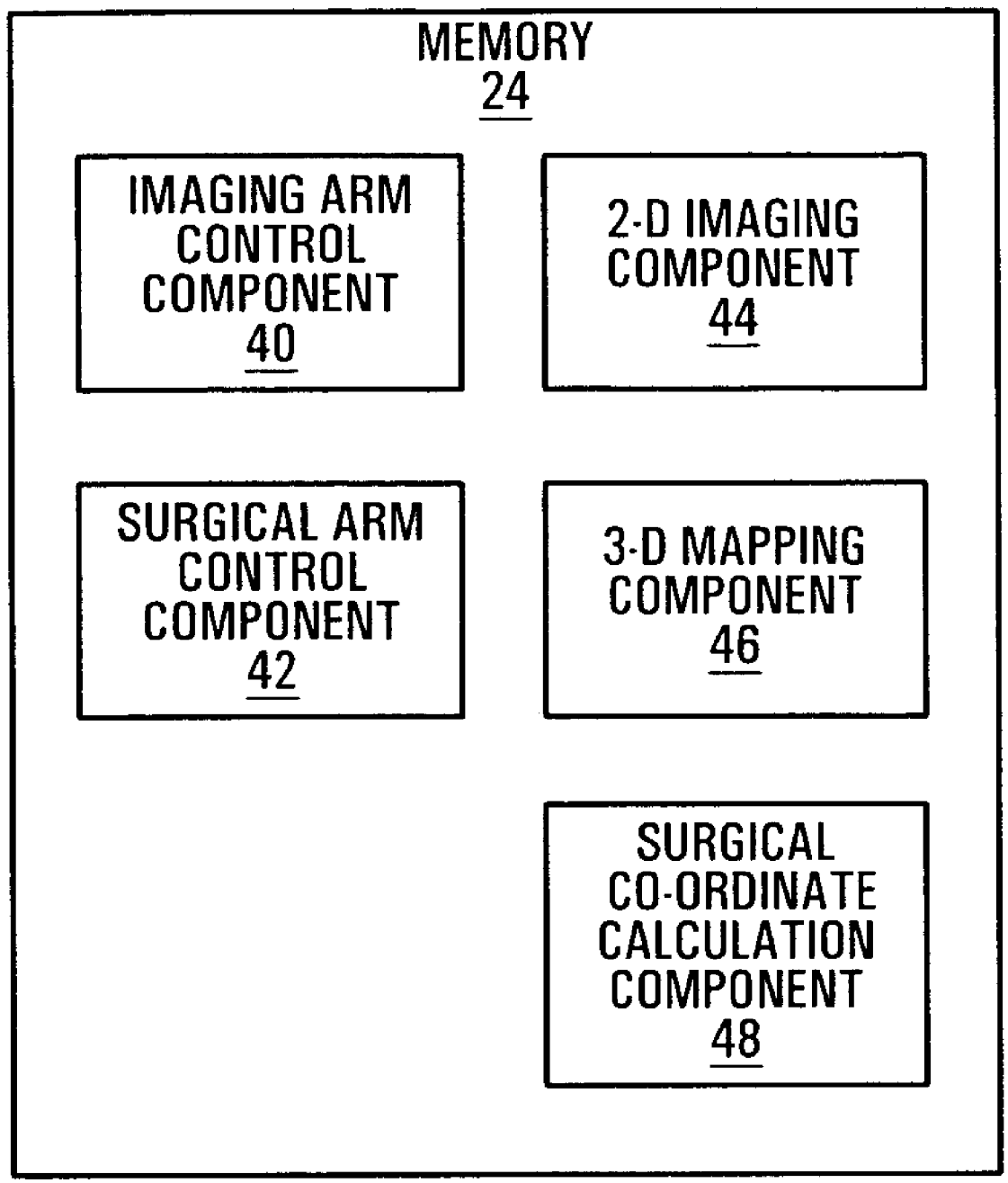
FIG. 2 is a block diagram of software stored at a computing device of the apparatus of FIG. 1, exemplary of embodiments of the present invention.

Software components stored within memory 24 are further illustrated in FIG. 2. As illustrated, memory 24 stores an imaging arm control software component 40 for controlling the motioning and position of arm 12; a surgical arm software component 42 for controlling the motioning and position of surgical arm 16 and surgical instrument 18; a 2-D imaging component 44 for receiving and processing 2-dimensional scanned data from imaging probe 14; a 3-D mapping component 46 for assembling 2-D imaging data into a 3-dimensional model of the scanned region; and an surgical co-ordinate calculation component 48 for calculating a incision points and excision locations for surgically removing a breast anomaly, as detailed herein. Each of software components 40-48 may be formed using conventional programming techniques and libraries. Their function and structure will become apparent. Other conventional software components, such as operating system software, libraries and the like are not specifically illustrated.

Figure 3:
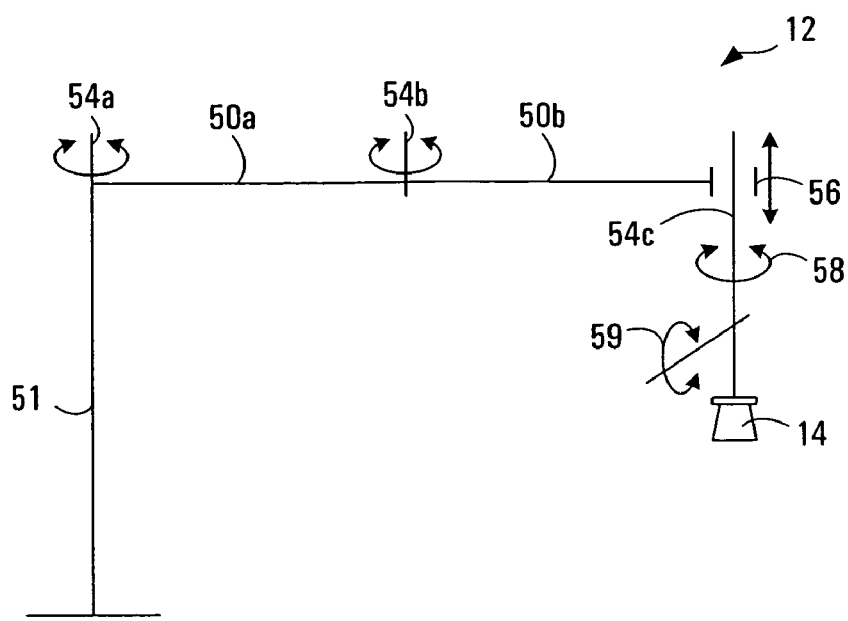
FIG. 3 is a simplified schematic diagram of an imaging arm and imaging probe of the apparatus of FIG. 1, indicating the rotational and translational degrees of freedom of the arm and probe.

Robotic imaging arm 12 is further schematically illustrated in FIG. 3. As illustrated in FIGS. 1 and 3, imaging arm 12 includes two robotic arm sections 50a and 50b, mounted to an upwardly extending base 51. As illustrated, robotic arm section 50a is mounted at its end to upwardly extending base 51, by joint 50a that allows rotation of arm 50a about a vertical axis. Robotic arm section 54b is mounted to robotic arm 50a by joint 54b that similarly allows rotation of one end of arm 50b about a vertical axis. A shaft 58 extends vertically downwards from the end of arm 50b, and is mounted on a linear actuator 56, allowing motion of shaft 58 in an up and downward direction. Linear actuator 56, further includes a rotational joint 54c, allowing rotation of shaft 58 about its lengthwise extending axis. Finally, imaging probe 14 is mounted to the end of shaft 58 by rotational joint 59, allowing rotation of an axis in the horizontal plane. Each of joints 54a, 54b and 54c includes a servomotor that receives control input from computing device 20. Each joint 54a, 54b, and 54c further includes a position encoder, which may be read by computing device 20 to assess the exact angular orientation of each of joint 54a, 54b, and 54c allowing computing device 20 to calculate the orientation and location of the robotic imaging arm 12 and thus imaging probe 14 at any given time.

Exemplary robotic imaging arm 12 thus has five degrees of freedom. Preferably, the imaging probe 14, in combination with robotic imaging arm 12, may sample any position in 3-D space in proximity to the patient, allowing the region of the breast tissue comprising abnormal tissue may be completely scanned.

Imaging probe 14 may be any device that can scan a patient or a region of a patient's body and produce a 2-D image of the scanned region. For example, the imaging probe 14 may be an ultrasound probe or, an x-ray device as used in conventional mammography devices. Such imaging probes are known to a skilled person. In a preferred embodiment, the imaging device may include a linear or sector ultrasonic sensor, as available commercially.

Imaging probe 14 is in communication with computing device 20, and sends the scanned image information for processing by 2-D imaging component 44 at computing device 20. In the depicted embodiment, imaging probe 14 scans images in the plane of orientation of probe 14.

Figure 4:
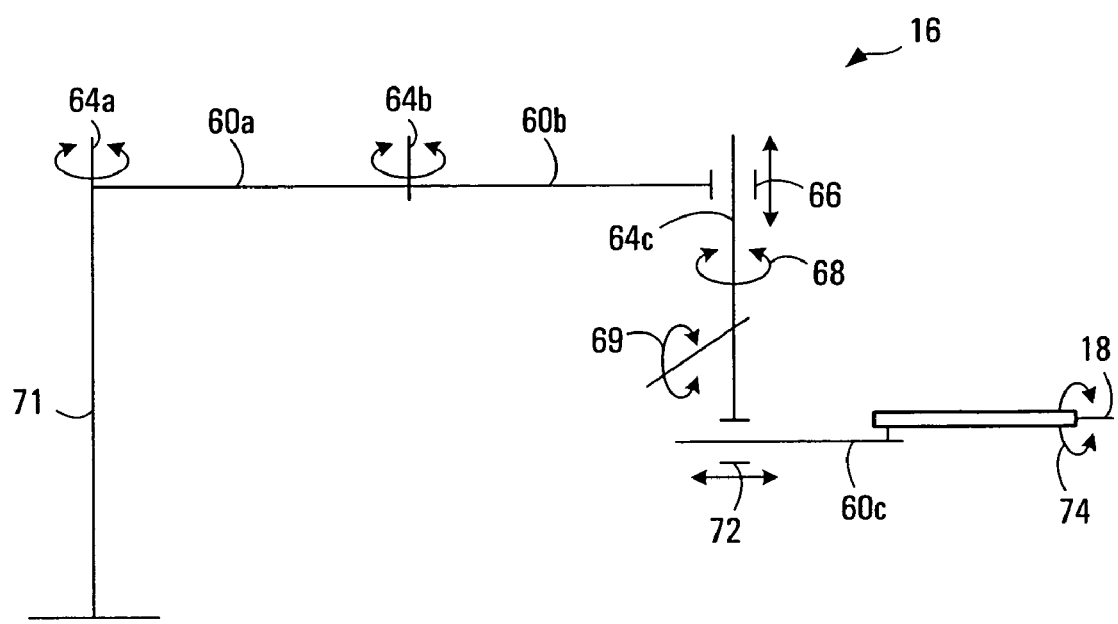
FIG. 4 is a simplified schematic diagram of a surgical arm and surgical instrument for tissue removal, of the apparatus of FIG. 1, indicating the rotational and translational degrees of freedom of the arm and device.

Apparatus 10 further include robotic surgical arm 16 and tissue removal instrument 18, more particularly illustrated in FIG. 4.

Surgical instrument 18 may be a device suitable for excising a region of tissue from a patient's body, in an automated, minimally invasive manner. For example, the device may be adapted to create an incision in the skin of a patient, and then, by inserting a blade, needle or other cutter into the incision, may be capable of excising a tissue portion. Such devices may include biopsy devices, including a minimally invasive device, for example, as commercially available core needle device or a vacuum assisted biopsy device. The latter is illustrated in the preferred embodiment.

The surgical instrument 18 may be any biopsy device, as would be understood by a skilled person. Example devices are disclosed in U.S. Pat. Nos. 6,213,957, 5,595,185 and 6,019,733, the contents of which are herein incorporated by reference.

A core needle biopsy device includes a hollow needle that can be inserted through the skin to the abnormal tissue. Typically, the barrel of the needle is fitted with a cutting mechanism that may excise a tissue sample. A vacuum assisted biopsy device includes a hollow probe that uses a vacuum to gently draw tissue into a tissue-receiving chamber. A cutting mechanism is used to excise a tissue sample.

The exemplified surgical instrument 18 may have a motor driven cutting mechanism that can be moved longitudinally within the hollow probe.

In the exemplified embodiment, surgical instrument 18 is a vacuum assisted biopsy device, having a hollow needle and an aperture in the sidewall of the needle. Excised tissue may thus be collected using suction.

Further, in the depicted embodiment, robotic surgical arm 16, depicted in FIGS. 1 and 4, is similar in design to robotic imaging arm 12, having arm portions 60a and 60b, mounted to upwardly extending base 71 by joint 64a and to each other by joint 64b. Again, each joint 64a, 64b includes a servomotor and a position information encoder, each in communication computing device 20, providing information for processing by a surgical arm control component 42. A shaft 68 is mounted proximate the end of arm portion 60b by a linear actuator 66, and for rotation about its axis by joint 64c. Actuator 66 allows up and down motion of shaft 68. Joint 64c also includes a servo motor and position encoder.

A further rotational joint 69 connects arm portion 60c at its end to shaft 68. A linear actuator 72 further connects surgical instrument 18 to arm portion 60c. Finally, surgical instrument 18 includes a further rotational joint 74 allowing rotation about the axis of the surgical instrument 18 and allowing for the positioning of the aperture in a desired position to access the tissue that is to be excised and then removed through the aperture by the application of a vacuum and the actuation of a cutting device located within the bore of the needle, under control of computing device 20.

Exemplified robotic surgical arm 16 thus has seven degrees of freedom, so as to allow it to access any point in 3-D space adjacent to the region of tissue scanned by imaging probe 12. Preferably, the surgical instrument 18 can be translated and rotated about its longitudinal axis, providing an additional two degrees of freedom, and allowing surgical instrument 18 to access and excise tissue from any point in the scanned region of the patient's body, preferable from within a region of the patient's breast.

As should now be apparent, arm portions 50a, 50b and 60a, 60b lie in a plane. This facilitated counterbalancing of arms 12 and 16. As well, torques required for actuators of joints 54a, 54b and 64a, 64b is reduced.

As will become apparent, apparatus 10 uses a common Cartesian co-ordinate system to define locations of the end of each arm 12 and 16, imaging probe 14 and the tip of tissue removal instrument 18.

Figure 5:
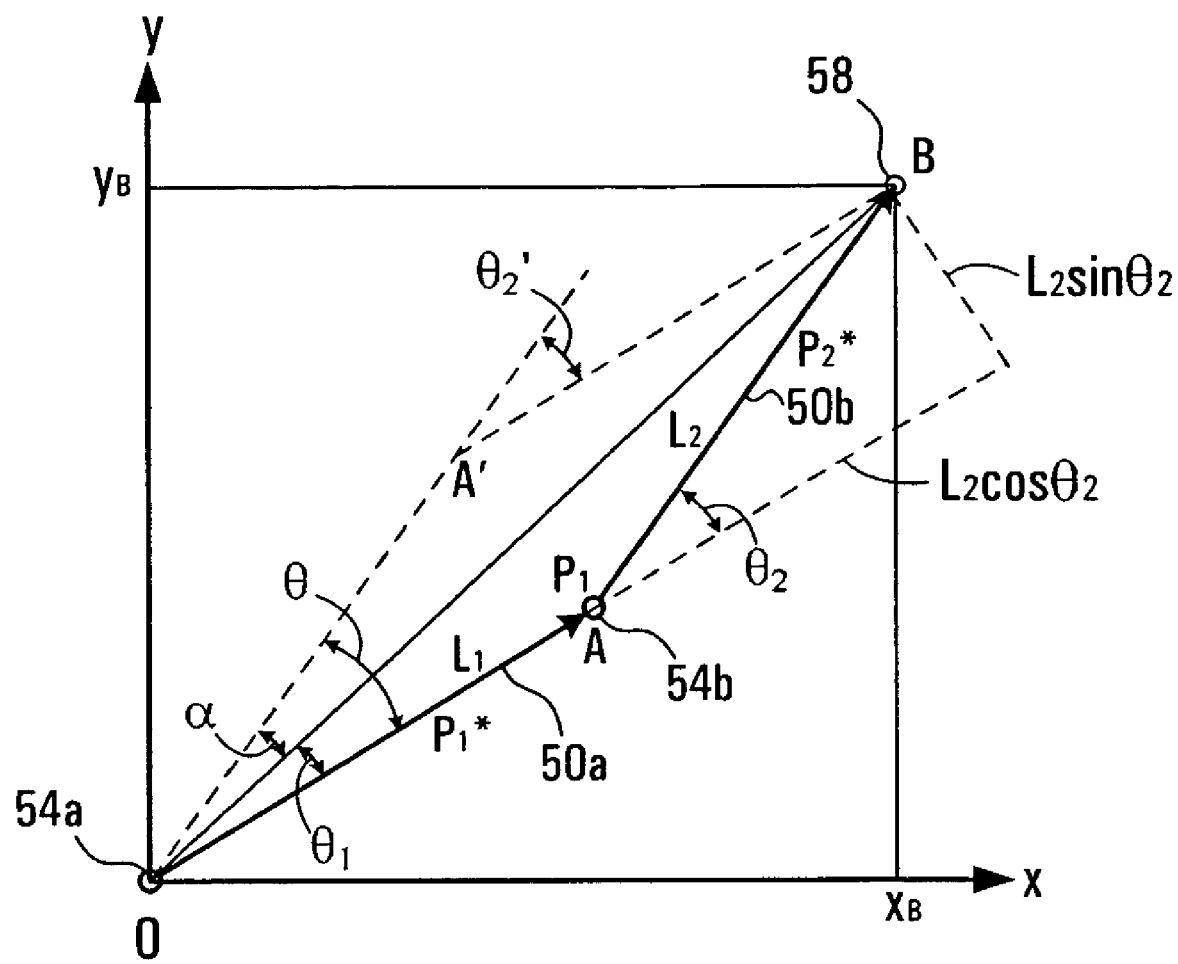
FIG. 5 is a schematic diagram, detailing calculation of the position of the imaging arm of FIG. 1.
Figure 6:
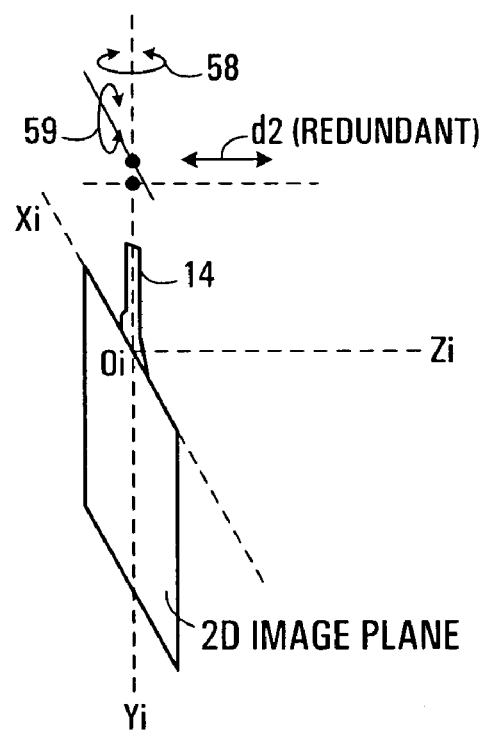
FIG. 6 is a schematic diagram illustrating the articulation of the imaging probe of the imaging arm of FIG. 1.
Figure 7:
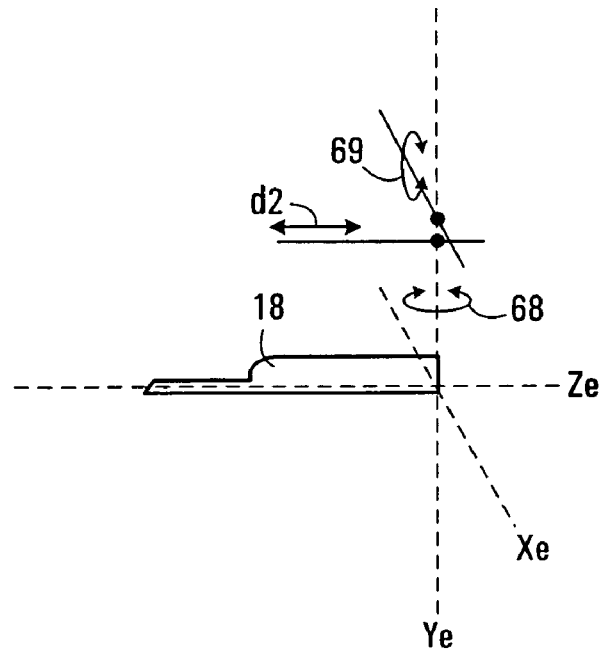
FIG. 7 is a schematic diagram illustrating the articulation of the surgical instrument of the surgical arm of FIG. 1.

Translation of joint positions to Cartesian co-ordinates may best be appreciated with reference to FIGS. 5 to 7. FIG. 5 illustrates the arm portions 50a and 50b of arm 12, modelled as vectors $P_1^*$ & $P_2^*$ starting from the proximal (closest to the coordinate frame origin O) to the distal (closest to the end effector B) points. Here, O is the origin of the robot co-ordinate for both the manipulator and the axis of joint 54a. Similarly, point A is the axis of joint 54b and B is the axis of the joint 54c. $\theta_1$ and $\theta_1$ are the values of the joint 54a and joint 54b. $l_1$ and $l_2$ are the lengths of arm portions 50a and 50b.

So, matrix expressions for the link vectors for the manipulator are, $$p_1^* = l_1 \begin{pmatrix} \cos\theta_1 \\ \sin\theta_1 \end{pmatrix}$$

$$p_2^* = l_2 \begin{pmatrix} \cos(\theta_1 + \theta_2) \\ \sin(\theta_1 + \theta_2) \end{pmatrix}$$

Link position vectors in the stationary reference frame with their origin at the joint 54*a* are designated as $P_i$ for the ith link.

$$P_1 = P_1^* \,\&\, P_2 = P_1^* + P_2^*$$

The position of the shaft 58 of arm 12 is the output of the direct kinematic analysis or, input of the inverse kinematics, expressed as:

$$P_2 = (x_B, y_B) \text{ or,}$$

$$p_2 = \begin{pmatrix} x_B \\ y_B \end{pmatrix} = \begin{pmatrix} l_1\cos\theta_1 + l_1\cos(\theta_1 + \theta_2) \\ l_1\sin\theta_1 + l_1\sin(\theta_1 + \theta_2) \end{pmatrix}$$

or $$\begin{pmatrix} x_B \\ y_B \end{pmatrix} = \begin{pmatrix} (l_1 + l_2\cos\theta_2)\cos\theta_1 - l_2\sin\theta_2\sin\theta_1 \\ (l_1 + l_2\cos\theta_2)\sin\theta_1 + l_2\sin\theta_2\cos\theta_1 \end{pmatrix}$$

This can also be expressed in polar co-ordinates P and θ. The square of magnitude of positive vector $p=p^2$ is, $$p^2 = x_B^2 + y_B^2$$
$$= (l_1 + l^2\cos\theta_2)^2 + (l_2\sin\theta_2)^2$$
$$= l_1^2 + 2l_1l_2\cos\theta_2 + l_2^2$$

$$\tan\alpha = \frac{l_2\sin\theta_2}{l_1 + l_2\cos\theta_2} \text{ as } \theta = \theta_1 + \alpha$$

$$\tan\theta = \frac{(l_1 + l_2\cos\theta_2)\sin\theta_1 + l_2\sin\theta_2\cos\theta_1}{(l_1 + l_2\cos\theta_2)\cos\theta_1 - l_2\sin\theta_2\sin\theta_1}$$

Joint positions for a desired location (x,y) of shaft 58, may similarly be calculated noting that, $$\cos\theta_2 = \frac{(x^2 + y^2) - (l_1^2 + l_2^2)}{2l_1l_2}$$

Thus, each solution from $\cos\theta_2$ represents two values for $\theta_2$ characterized by equal magnitude and opposite signs represented as the dotted lines. Since arms 12, 16 have the same geometry these two solutions (inward arm and outward arm with respect to the origin) may be used independently for each arm. As a default the inward arm solution is used for surgical arm 12 and the outward arm solution is for imaging arm 12 (as represented by the dotted line of FIG. 5).

Now, for calculating $\tan\theta_1$:

$$\tan\theta_1 = \frac{-(l_2\sin\theta_2)x + (l_1 + l_2\cos\theta_2)y}{(l_2\sin\theta_2)y + (l_1 + l_2\cos\theta_2)x}$$

Thus, these equations may be used to compute the image position reference in XY plane in case of imaging arm 12 and later fed to the surgical arm 16 for positioning. Arm position in Z-direction is a direct calculation of the vertical joint variable for joint 56 (or 66).

The wrist unit for both arms 12 and 16 provide a spherical workspace for the end-effectors. To simplify the kinematic model, each wrist is decoupled to generate pitch, yaw and linear axes.

The kinematic diagram of the wrists of imaging arm 12 and surgical arm 16 are shown in FIGS. 6 and 7. The yaw (T3) and pitch (T4) angle for the surgical arm 16 is calculated from the projection of the axis of incision on XZ and YZ planes.

During initialization actuators 56, 66 and 72 are fully retracted. For both arms, the wrist is aligned horizontally and through T3 and aligned with arm through T4 and set to 0°. The needle aperture window is aligned and T5 is set to 0°.

Figure 8:
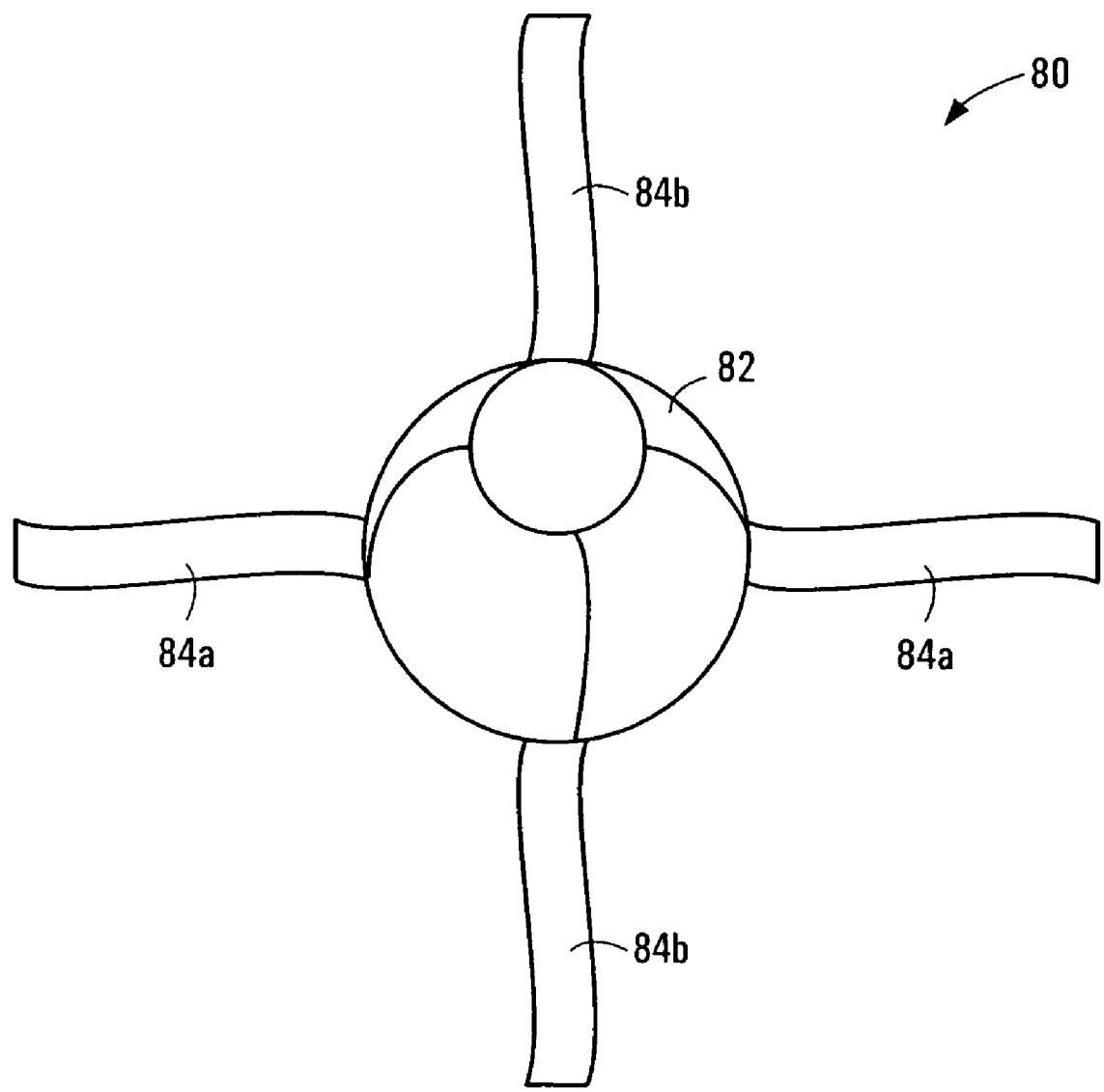
FIG. 8 is top perspective view of a breast holder, for restraining tissue in a patient.

FIG. 8 illustrates an exemplary holding cup 80 used to restrain motion of the breast during an excision procedure exemplary of an embodiment of the present invention. Holding cup 80 prevents shifting of the tissue, including the abnormal tissue to be excised. During the course of the procedure, the breast tissue may move, due to breathing, or other movement of the patient. Therefore, the breast tissue is restrained so as to minimize movement of the breast, such that the abnormal tissue will occupy approximately the same space throughout the procedure.

Exemplary holding cup 80 is a cup or other shape designed to tightly compress the breast tissue. The holding device is preferably constructed of a rigid or semi-rigid material, for example, stainless steel mesh 82 that can be penetrated by a surgical needle or probe. As will be apparent, the finer the mesh 82, or the more penetrable the material generally, the less likely it is that the holding cup 80 will interfere with the sampling of 3-D space by tissue removal instrument 18. At the same time, the material should be strong enough to secure the breast from movement during the tissue removal process.

Holding cup 80 may be lined with a membrane (not shown) to protect the skin of the patient, for example, with a latex membrane. Conveniently, the latex membrane holds the breast in position with a comfortable tightness to reduce unpredictable mobility of tissue during excision. Further, latex is transparent to ultrasound and typically does not deteriorate the image for the purpose of surgical guidance. Skin along with the membrane is pierced with the needle while making initial incision.

Holding cup 80 may be attached to the patient, for example, with straps 84*a* and 84*b*. In the embodiment depicted in FIG. 4, the device has one longitudinal strap 84*a* and one lateral strap 84*b* relative to the patient body. In use, the straps are secured around the patient so as to restrain the breast tissue, while minimizing discomfort to the patient.

Alternatively, a breast may be held by another holding device such as a pair of parallel compression plates, as for example typically used in mammography. This alternative embodiment allows for x-ray based scanning of the breast. The plates are used to compress the breast so as to make the abnormalities visible under x-ray imaging. Apparatus 10 may easily be used with such a holding and imaging device, however, the excision may be restricted to planes lying between the compression plates. Intermittent x-ray imaging, similar to that used in stereotactic breast biopsy is suggested for this method.

Figure 9:
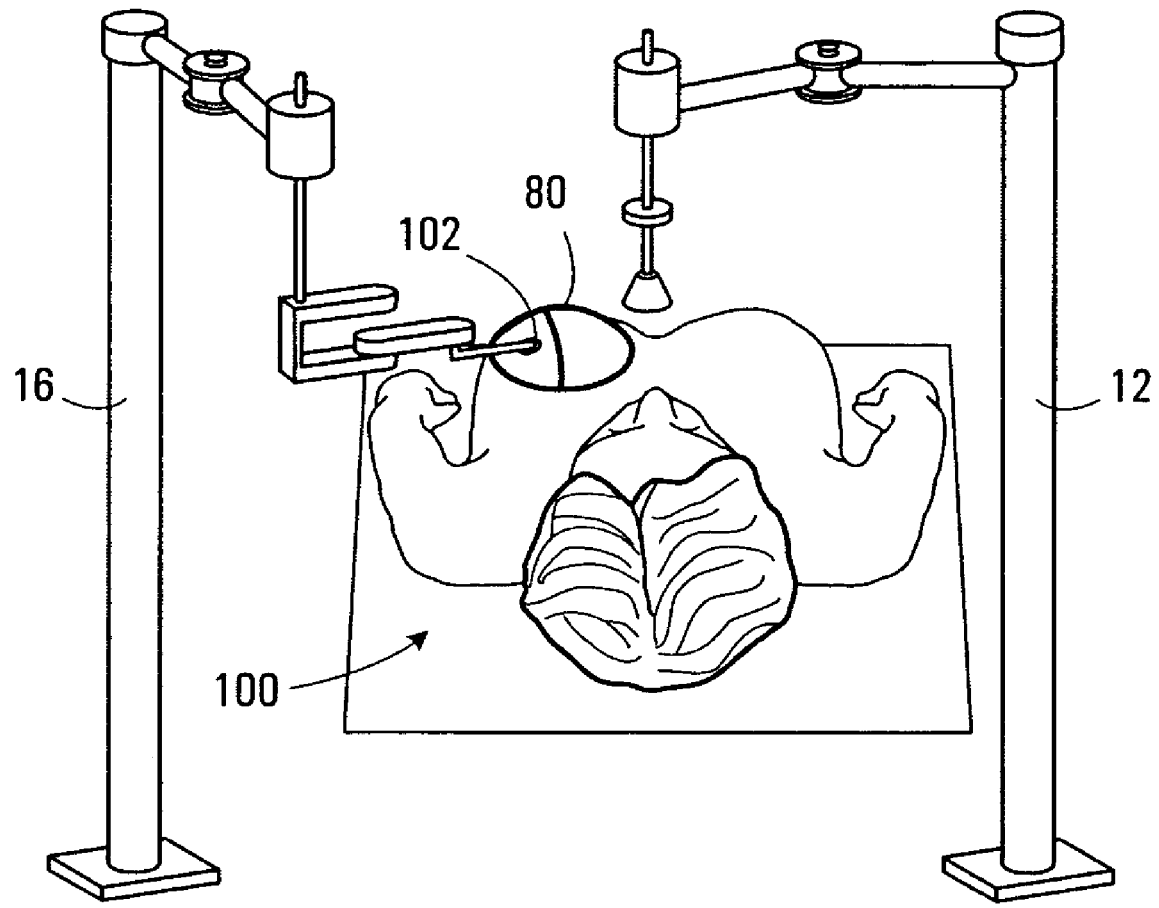
FIG. 9 is an illustration of an example of the apparatus of FIG. 1, in use.

In operation, a patient 100 is placed on an operating platform as illustrated in FIG. 9. As can be seen in FIG. 9 the patient is lying face up (supine position). The breast is restrained by cup 82. This allows imaging arm 12 with imaging probe 14 to scan the breast from above, and further surgical arm 16 to guide cutting instrument 18 to various incision and excision positions. Of course, the patient may be positioned upright, or lying down in a face down position (prone position). For example, the patient could lie face down, with the breast protruding through an aperture in the surface on which the patient is positioned.

Figure 10:
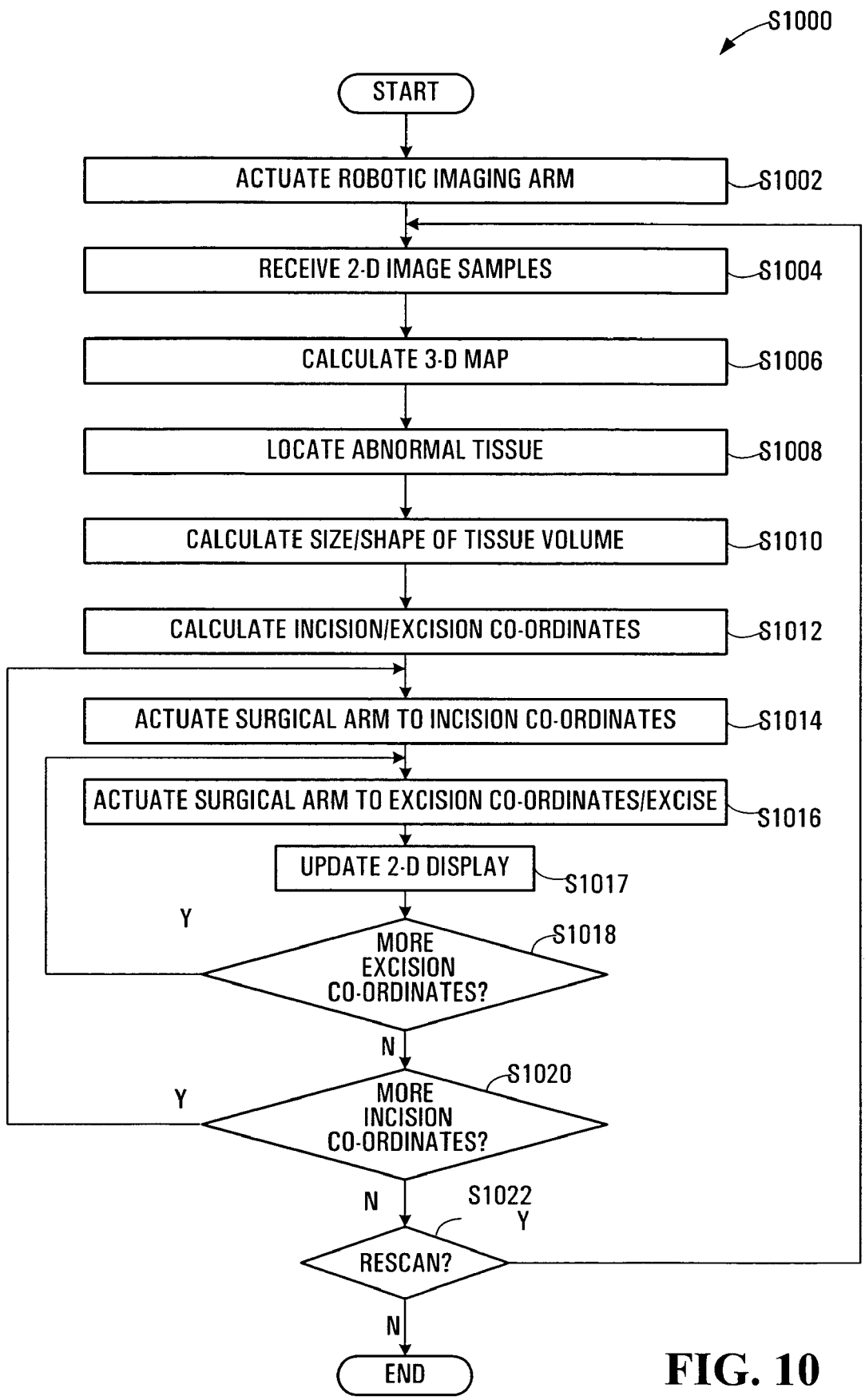
FIG. 10 is a flow chart illustrating steps performed by the apparatus of FIG. 1, exemplary of an embodiment of the invention.

Apparatus 10 under software control performs steps S1000 depicted in FIG. 10, to detect and surgically removal abnormal breast tissue, for example, as would be removed in a lumpectomy.

In step S1002, computing device 20 under imaging control arm control component 40 (FIG. 2) actuates the robotic imaging arm 12 and energizes imaging probe 14 to scan all or a portion of the patient's breast. The portion of the breast may be specified by operator input. Imaging arm control component 40 causes imaging probe 14 to move through a defined region of 2-D space adjacent the patient's breast and take a series of 2-D images. For example, imaging arm control component 40 may sweep the imaging probe 14 along an axis, causing acquisition of two dimensional images of the breast in the plane normal to this axis.

As noted, location of the surgical arm 16 and all the relative measurement of the position and orientation of imaging probe 14 and surgical instrument 18 are measured with respect to a common reference.

FIG. 5 thus shows the geometric representation of the position of the vertical shaft 58 of imaging arm 12 and shaft 68 of surgical arm 16 along the horizontal plane. Joint 56 of imaging arm 12 and joint 66 of surgical arm 16 moves the horizontal plane upward or downward. FIG. 6 shows the image plane of the imaging probe 14 relative to the arm portion 58 and joint 54c and 59. Similarly FIG. 7 shows the surgical instrument 18 relative to the surgical arm portion 68 and joints 64c, 69, 72 and 74.

In step S1004, the two-dimensional (2-D) images are received at computing device 20 from the imaging probe 14, and processed by 2-D imaging component 44.

Figure 11:
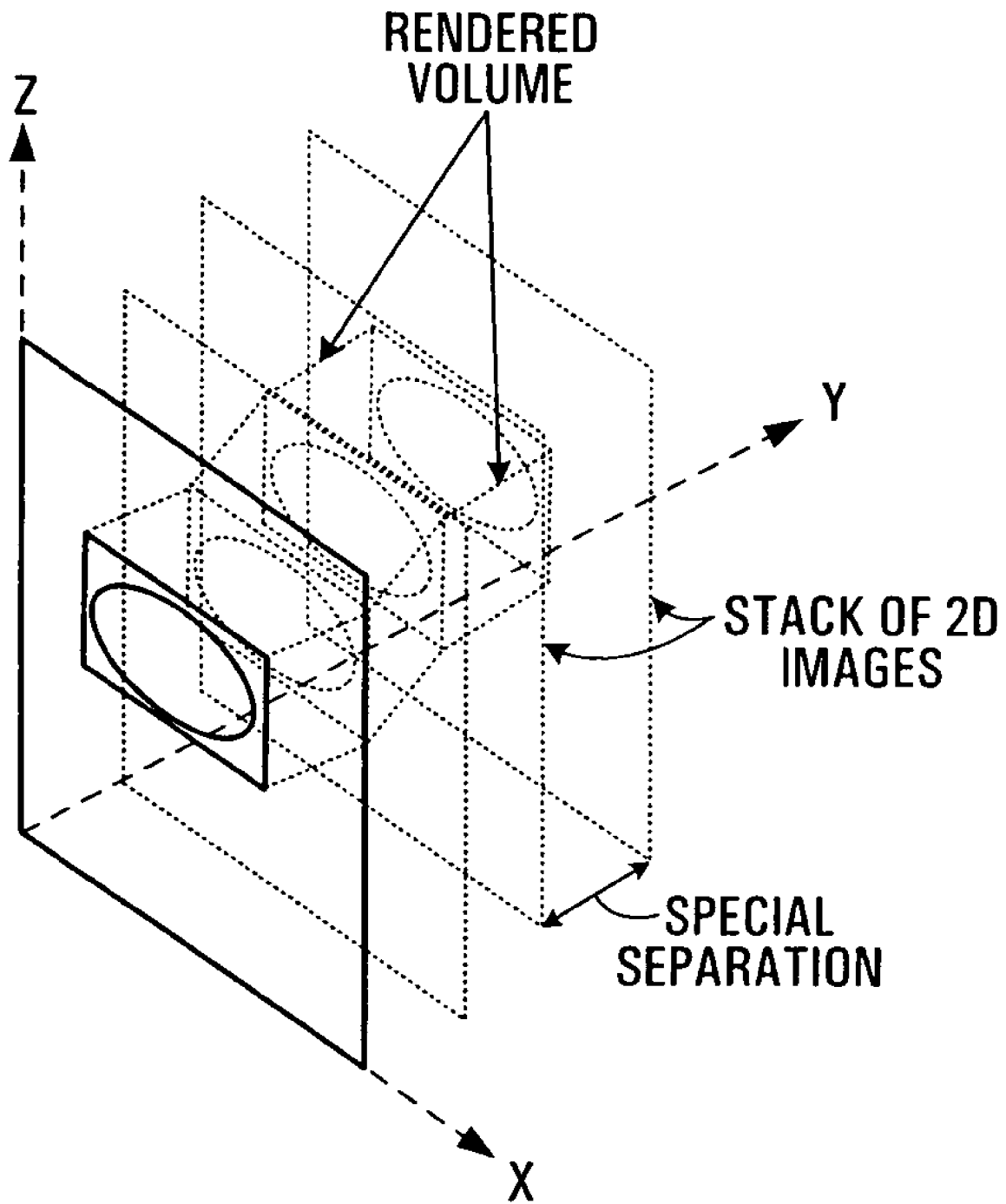
FIG. 11 is a diagram illustrating image acquisition using the apparatus of FIG. 1.

Once 2-D scanning data is acquired, computing device 20 under control of 3-D mapping component 46 calculates a 3-dimensional map of the scanned breast in step S1006. Specifically, computing device 20 compiles the 2-D images received and processed by 2-D imaging component 44 so as to generate a 3-D volume of the affected region. For example, the 3-D volume may be determined by stereotactic methods. Alternatively, the 3-D image may be determined by taking multiple 2-D images in parallel planes, with a given distance between the planes, as for example illustrate in FIG. 11. The compilation may include interpolating information between the 2-D planes. Knowledge of the co-ordinates of the imaging probe 14 for each 2-D image allows accurate re-construction of the scanned tissue in 3-D.

Once a 3-D map has been calculated, computing device 20 under control of surgical co-ordinate calculation component 48 calculates incision and excision coordinates required for the surgical instrument 18 to perform an incision followed by a series of excisions so as to excise the abnormal tissue. That is, computing device 20 under control of surgical co-ordinate calculation component 48, based on the 3-D, locates the abnormal tissue within the 3-D image in step S1008 and calculates the size and orientation of the volume of tissue to be excised shape of the tissue to determine the excision coordinates in step S1010.

Various image-processing algorithms may be used in step S1008 to accurately detect the edge of the breast tumour in the ultrasonic images captured in step S1004 and mapped in step S1006. Example algorithms include known watershed segmentation, non-rayleigh statistics, neural networks, texture analysis and the like.

In any event, the edges of the breast tumour are used to assess a volume of tissue to be excised. As there is typically limited control over the shape and size of the excised tissue sample due to limited size of cutter, the tissue is not exactly removed within the tumour boundary. As such, in the disclosed embodiment, a volume of interest having a regular geometric shape that encapsulates the entire tumour is assessed in step S1010. In the disclosed embodiment, a cylindrical excision region is illustrated. Conveniently, a cylindrical shape suits a rotating needle of surgical instrument 18. However, other regular geometric shapes such as a rectangular prism or other shapes befitting and encapsulating a given tumour dimension may also be used.

The dimensions and co-ordinates of the volume of interest are derived from the 3-D image map in step S1004. As well, a 2-D reference image may be assessed. That is, the 2-D cross-section of the tumour having the largest dimension may be considered as the reference image. Four extreme points on the visible tumour on the reference image identify the boundary of the tumour.

For use during surgery, a series of additional 2-D images with a known internal spacing along the full maximum length may optionally be taken along the plane normal to the reference image (cross-section plane perpendicular to reference image plane) plane.

Similarly, four extreme points representing the boundary of the tumour on these images may be used to find or verify the maximum dimension of the tumour. This may provide the third dimension (depth) for volume estimation.

Tumour location is calculated from the Cartesian co-ordinates of the tumour, based on the position of the imaging probe as the 2-D images are acquired. The cylinder is identified by its diameter, length and axial orientation.

The parameters for the cylindrical tumour volume calculation are

Length→Maximum dimension from reference image

Diameter→Maximum dimension among all 2-D cross-sectional images

The parameters for the volume of interest, which includes the margin amount, are Total-Length→Length+2×margin Total-Diameter→Diameter+2×margin Alternatively, a simplified approach to generate a boundary may be based on a surgeon's selection of four extreme points (2 points in each dimension) on the region of interest covering the suspected tumour on each image. Volumetric information may be generated by linearly scanning the ultrasound transducer across the affected surface in a given direction as shown.

Imaging probe 14 may be moved manually to the suspected region and scanned manually by moving the imaging arm (all joints are back drivable to manually move and can be locked at any configuration using mechanical and servo lock) to obtain the image showing best possible view of the tumour or suspicious mass. The best possible view corresponds to show the maximum spreading of the tumour horizontally and vertically with respect to the image plane. After selection of points on the reference image the transducer is rotated by 90° to show the cross-sectional view of the suspected area or tumour. The transducer is moved linearly along the scan axis with small increment (typically 2 mm) to acquire images showing the cross sectional views of the tumour. Similar to the reference image, four points are selected on each image showing the tumour.

Each selected point carries x and y values which correspond to the absolute location on the tumour as they are converted from the screen coordinate which is in number of pixel to corresponding millimeter on their respective image. The difference between the minimum x and maximum x out of all selected points with respect to the screen represents length of spread of the tumour along Zi-axis. Similarly, the difference between minimum y and maximum y out of all selected points represents the length of spread of the tumour along Yi-axis. Extreme points on the images may be marked through input provided by surgeon to computing device 20, through for example keyboard 38.

Out of these two values, the maximum and minimum dimensions may be taken as the length and diameter of cylinder respectively and the cylinder volume may be calculated. The margin amount is specified by the surgeon and added accordingly to the dimensions of the cylinder to calculate the total excision volume.

Subsequently, the number of cuts required for complete excision of the tumour is calculated based upon a given cutter window size in step S1012. In the disclosed embodiment, the incision is made along an axis that is parallel to the axis of the cylinder defining the volume of interest.

Specifically, based on the abnormal tissue volume, surgical coordinate calculation component 48 can then calculate the coordinates required for the incision and excisions to be performed by surgical instrument 18 in step S1012.

As noted, a margin of healthy tissue is included in the calculations in step S1010, so as to increase the probability of capturing most of the abnormal tissue, including tissue at the periphery of the abnormality, which may be abnormal but may not appear so based on the scanned image. For example, a 1 cm perimeter of apparently healthy tissue may be included in the calculation.

In step S1012, computing device 20 under control of coordinate surgical co-ordinate calculation component 48 calculates the coordinates for one or more incision to be made by tissue removal instrument 18, and the coordinates for a series of excisions to be made from that incision point where the cutting device of the tissue removal device is inserted in the breast tissue. That is, the calculated excision volume includes a central axis.

In most cases, only a single incision is required for surgery, however, multiple possible incision coordinates may be calculated in step S1012 and presented to a surgeon for a decision, as a mechanically feasible and optimum incision may not always be clinically optimum due to some clinical complications, for instance, very close to chest wall, lymph nodes, etc. Also, some larger tumour lumps (e.g. larger than stage 2 and spread) may also require multiple incisions In any event, the approach axis of surgical instrument 18 is calculated in step S1012. In one embodiment, the central axis of the cylinder is used as the approach axis. Similarly, if rectangular prism is used, its central axis could be used as the approach axis. Accordingly, the intersection of this central axis and the surface of the breast is used as the point of incision.

Thus, the cutting needle of the surgical instrument 18 is placed at the center of the tumour and the tissue is progressively removed from all around in a symmetrical manner.

As well, the number and orientation of excisions that are to be made are calculated. The calculation is performed based in part on the capacity of a surgical device that is to be used to remove the tissue and based in part on the placement of the abnormal tissue with respect to the breast. Specifically, each excision is assumed to excise tissue along a length $L_x$. $L_x$ may be assessed empirically and depends on the length of the opening of the excision device and the strength of the vacuum.

Figure 12:
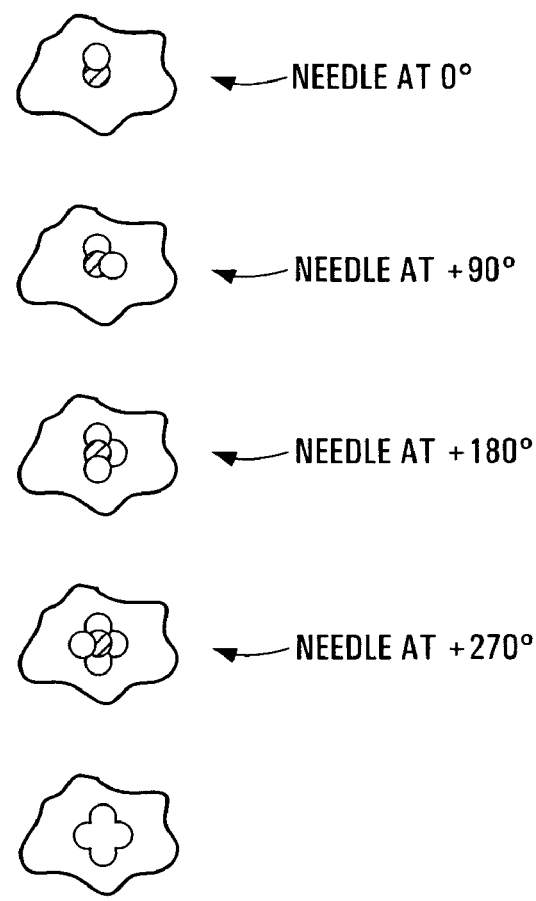
FIGS. 12 and 13 schematically illustrates a tissue removal method using a surgical instrument of the apparatus of FIG. 1.

Moreover, each excision is assumed to excise tissue within a region parallel to the incision axis and within a defined distance of the axis. Thus, excisions at four angular positions, at 90° spacings, and corresponding to a single axial position allows excision in a generally cyclindrical volume having length $L_x$. This is illustrated in FIG. 12.

Figure 13:
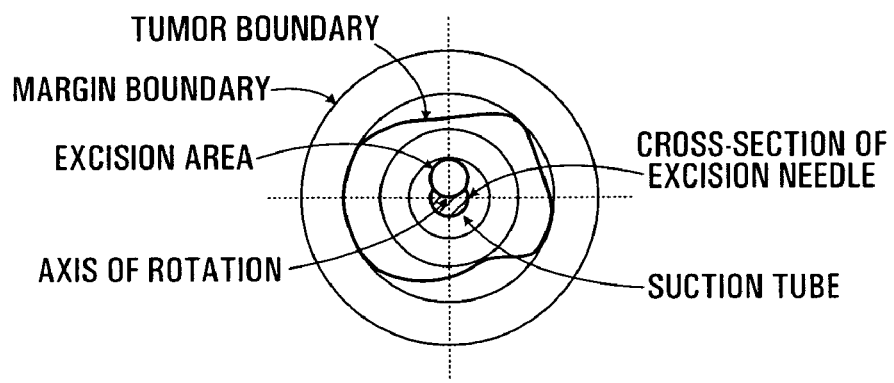

As tissue is assumed to collapse into the void created by the excision, additional excisions at the same location, allows excision of a cylinder of larger diameter of length $L_x$. The number of rotations of the blade of surgical instrument 18 is thus calculated in dependence on the diameter of the diameter of the cylinder to be excised. Each rotation of the blade is thus assumed to excise an additional annulus about the central axis, as illustrated in FIG. 13.

However, as the effect of gravity and compression may be less on the sides of volume to be excised, this method may not be accurate if the tumour size is too large (e.g. larger than 2 cm as the largest dimension with a 4 cm diameter including the margin tissue on both sides). As such, multiple parallel incision axes may be calculated for any particular cylinder.

The surgical co-ordinate calculating component 48 thus provides set of Cartesian coordinates (x, y, z) representing an incision co-ordinates $I_1$ for the end of the robotic surgical arm 16, holding surgical instrument 18 to be positioned in 3-D space outside the breast at the appropriate position and angle for incision.

As noted, the center line of the cylinder determined in step S1012 used to encapsulate the tumour is used as the incision axis. The incision is effected by orienting the axis of surgical instrument 18 to align with incision axis in $X_I Z_I$ plane (by adjusting yaw and pitch (T4, T5) through joints 68, 69 and 74—vis FIGS. 5 and 7); and then orienting the axis of surgical instrument 18 to align with incision axis in $Y_I Z_I$ plane (d1, T3) through actuator 66 and joint 69; and moving the needle of surgical instrument 18 this axis.

The corresponding values for each of joints 68, 69 and 74 and actuator 66 of surgical arm 16 are thus calculated based on the projection of the incision axis on the excision arm co-ordinate frame.

The cutting point of the tissue removal device 22 is inserted through cup 82 and through the patient's skin to the site of the abnormal tissue. Preferably, the incision or incisions are minimally invasive so as to minimize scarring, preferably between 1 and 10 mm, more preferably between 1 and 5 mm in length.

Next, the surgical instrument 18 is moved to the initial excision position $E1_{I1}(d2, \theta)$ in step S1014, by adjusting joints 66 and 74 and cutting device is actuated to excise a volume of tissue. In the depicted embodiment, the cylinder of interest is excised at beginning at its deepest extreme from the point of incision. Step S1016 is repeated for all excision co-ordinates associated with incision co-ordinate $I_1$, as a result of step S1018. Specifically, for each radial position d2, the needle of surgical instrument 18 is rotated to the various angular positions. At each angular position, extractions of tissue are made by applying suction transmit through the window of surgical instrument 18. Next, the radial position (d2) of surgical instrument 18 is adjusted, based on the size of its cutting window. After all excisions at incision point $I_1$, are made, steps S1014 may be repeated for any additional incisions (e.g. additional incision axes), as assessed in step S1020.

During surgery, on-line guidance may be provided by apparatus 10. Pre-calculated coordinates may be replicated by the apparatus 10 on the display of computing device 20 and the reference 2-D image along the cylinder axis shows the needle and the target region and collapse of the tissue (along the axes of the cylinder) may be updated as the surgery progresses, in step S1017.

Thereafter, the area of interest may optionally be rescanned as determined in step S1022, by repeating steps S1004 and onward to assess additional incision and excision co-ordinates. Optionally, a surgeon's input (provided, by example, by way of an input device such as a keyboard 38 or, a light pen, or, mouse) may be sought in step S1022 to control re-scanning. This repetition of steps S1004 and onward after completion of excisions associated with each incision allows a surgeon to monitor the position of the abnormal tissue during the surgery. This is particularly useful if the abnormal tissue mass collapses or deforms during the surgery as the result of removal of a partial volume of the abnormal tissue, and helps to ensure that subsequent incisions properly target the abnormal tissue.

Figure 14:
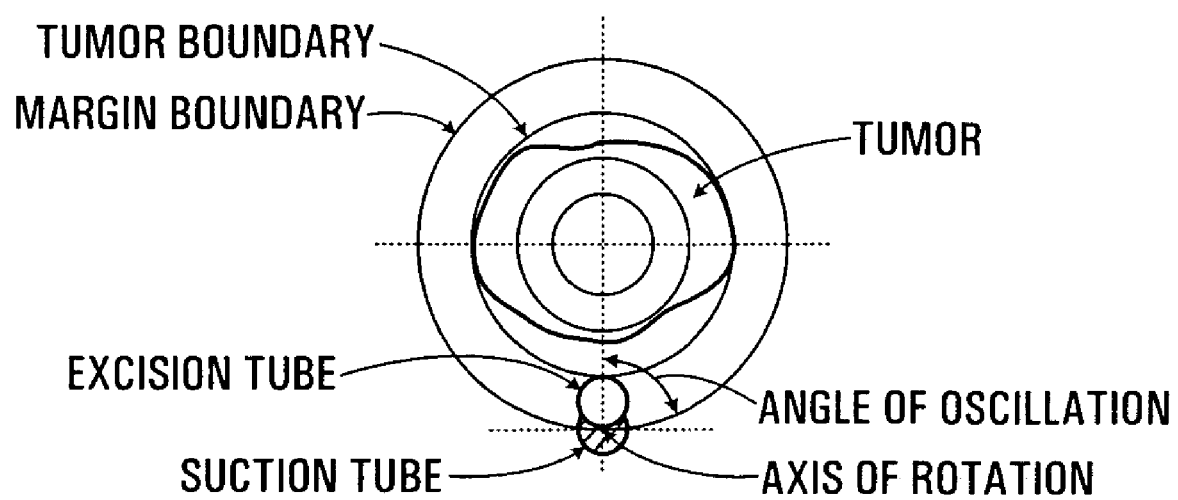
FIG. 14 schematically illustrates an alternative tissue removal method using a surgical instrument of the apparatus of FIG. 1

Alternatively, instead of positioning the blade of the surgical instrument 18 at the centre of the volume of interest, the suction window may be placed along another axis, such as a parallel axis at the lower boundary of the total tumour as shown in FIG. 14. This is possible for cylindrical volumes, rectangular prisms, and other shapes. This method takes advantage of the fall of tissue due to gravity as well as the external compression. However, instead of rotating the suction window by 360° in each stage, the needle may be oscillated within a range of angle, which is less than ±180°. This oscillation angle is based on the dimensions and shape of the tumour including the margin. The larger the tumour, the greater the oscillation angle.

As should now be appreciated, in the disclosed embodiment scanning and excision are performed by apparatus 10 in a mostly automated manner. However, apparatus 10 may be used in conjunction with input of a surgeon. For example, a surgeon can manually verify that incision is in the proper location, and can guide or assistant in the guidance of imaging probe 14 and surgical instrument 18. To this end, joints and actuators of the imaging arm 12 and surgical arm 16 may be manually manipulated, in addition to be being actuated by computing device 20. Of course, changes in position resulting from manual manipulation are sensed by computing device 20 for reference purpose or to be used further in computation of desired excision coordinates. Positions of surgical instrument 18 and imaging probe 14 may be presented in real time on the display of computing device 20. Similarly, incision and excision co-ordinates may be presented on this display.

As well, although the disclosed device and techniques are particularly well suited in breast surgery, they may easily be used in removing other lesions, in other regions of interest. For example, the device and techniques, appropriately modified, might be used in the removal of testicular lesions, or other lesions.

As can be understood by one skilled in the art, many modifications to the exemplary embodiments described herein are possible. The invention, rather, is intended to encompass all such modification within its scope, as defined by the claims.

What is claimed is:

1. A computer-assisted method of removing abnormal tissue from a region of interest by way of a reduced number of incisions, said method comprising:
   generating a three-dimensional (3-D) map of said region of interest comprising abnormal tissue;
   determining a tissue volume, based on said 3-D map, said tissue volume including the abnormal tissue and an adjacent margin of healthy tissue;
   determining, based on said tissue volume, at a computing device a surgical plan including at least one incision point and a series of associated excision points associated with said at least one incision point; and
   controlling movement of a surgical instrument used to excise tissue, to sequentially move to each of said at least one incision point and to each of its associated excision points and excise tissue, resulting in removal of said tissue volume;
   wherein at least one of said at least one incision point is associated with two or more excision points.

2. The method of claim 1, wherein said region of interest forms part of a breast.

3. The method of claim 2, further comprising restraining said breast.

4. The method of claim 1, wherein said determining a tissue volume comprises determining a volume having a regular geometric shape.

5. The method of claim 4, wherein said regular geometric shape comprises a cylinder.

6. The method of claim 5, wherein said incision point is along a central axis of said cylinder.

7. The method of claim 6, wherein said series of excision points comprises a plurality of axial positions along said central axis.

8. The method of claim 7, wherein said series of excision points comprise a plurality of angular positions associated with each of said axial positions.

9. The method of claim 8, wherein a number of angular positions associated with each of said axial positions depends on a diameter of said cylinder.

10. The method of claim 7, wherein at least some of said series of excision points are at the same axial position along said central axis, and the tissue is assumed to collapse into a void created by said excisions.

11. The method of claim 6, wherein said surgical instrument comprises a vacuum assisted biopsy device.

12. The method of claim 5, wherein said incision point is along an axis parallel to a central axis of said cylinder, proximate an edge of said cylinder.

13. The method of claim 5, further comprising, repeating said generating, and said determining a tissue volume.

14. The method of claim 4, wherein said regular geometric shape comprises a rectangular prism.

15. The method of claim 14, wherein said incision point is along an axis parallel to a central axis of said rectangular prism.

16. The method of claim 1, wherein said generating comprises generating said 3-D map from a plurality of 2-D images of said region of interest.

17. The method of claim 1, wherein said determining a tissue volume comprising using edge detection of said 3-D map to locate boundaries of the abnormal tissue.

18. The method of claim 17, wherein said tissue volume is approximated as a cylinder encapsulating the abnormal tissue and a margin of normal tissue on all edges of the abnormal tissue.

19. The method of claim 1, wherein the abnormal tissue is a tumour.

20. The method of claim 1, wherein said series of excision points is determined assuming the tissue collapses into a void created by said excisions.

21. An apparatus for tissue removal comprising:
   a robotic imaging arm for holding and moving an imaging probe;
   a robotic surgical arm for holding and moving a surgical instrument suitable for tissue removal;
   a computing device for controlling movements of said robotic imaging arm, said imaging probe, said robotic surgical arm and said surgical instrument, said computing device operable to
      generate a three-dimensional (3-D) map of a region of interest in a patient, said region of interest comprising abnormal tissue;

determine a tissue volume, based on said map, said tissue volume including the abnormal tissue and an adjacent margin of healthy tissue;

determine a set of coordinates including an incision point and a series of at least two excision points associated with said incision point to move a tissue removal device to said incision point and from said incision point to said series of excision points and excise tissue to remove said volume, resulting in removal of the abnormal tissue using a reduced number of incision points.

22. The apparatus of claim 21, wherein said surgical instrument is a vacuum assisted biopsy device.

23. The apparatus of claim 22, further comprising a holder for restraining movement of tissue comprising the abnormal tissue.

24. The apparatus of claim 21, wherein said computing device further determines said tissue volume as a regular geometric shape.

25. The apparatus of claim 24, wherein said regular geometric shape comprises a cylinder.

26. The apparatus of claim 25, wherein said computing device determines said incision point along a central axis of said cylinder.

27. The apparatus of claim 26, wherein said computing device determines said series of excision points as a plurality of axial positions along said central axis.

28. The apparatus of claim 24, wherein said regular geometric shape comprises a rectangular prism.

29. A computer readable medium storing processor executable instructions which, when executed by a processor of a control system of a surgical apparatus comprising a robotic imaging arm for holding and moving an imaging probe; and a robotic surgical arm for holding and moving a surgical instrument, adapt said control system to:

generate a three-dimensional (3-D) map of the tissue comprising abnormal tissue;

determine a tissue volume in a patient, based on said map, said tissue volume including abnormal tissue and an adjacent margin of healthy tissue;

determine one or more incision points and a series of excision points associated with said incision points, based on said tissue volume to move a surgical instrument sequentially to said incision point and said series of excision points and excise tissue to remove said volume, resulting in removal of the abnormal tissue;

wherein at least one of said incision points is associated with two or more excision points.

30. A computer-assisted method of removing abnormal tissue from a region of interest by way of a reduced number of incisions, said method comprising:

generating a three-dimensional (3-D) map of said region of interest comprising abnormal tissue;

determining a tissue volume, based on said 3-D map, said tissue volume including the abnormal tissue and an adjacent margin of healthy tissue;

determining, based on said tissue volume, at a computing device at least one incision point and a series of associated excision points associated with said at least one incision point;

controlling movement of a surgical instrument used to excise tissue, to sequentially move to each of said at least one incision point and to each of its associated excision points and excising tissue, resulting in removal of said tissue volume;

wherein at least some of said series of excision points are at the same axial position along an axis through one of said at least one incision point, and said determining comprises accounting for the collapse of tissue into a void created by said excising.

* * * * *